US006811787B1

(12) United States Patent
Boyle et al.

(10) Patent No.: US 6,811,787 B1
(45) Date of Patent: Nov. 2, 2004

(54) OVER-EXPRESSING HOMOLOGOUS ANTIGEN VACCINE AND A METHOD OF MAKING THE SAME

(75) Inventors: Stephen M. Boyle, Blacksburg, VA (US); Silvio Cravero, Republica (AR); Lynette Corbeil, San Diego, CA (US); Gerhardt Schurig, Blacksburg, VA (US); Nammalwar Srirnaganathan, Blacksburg, VA (US); Ramesh Vemulapalli, Blacksburg, VA (US)

(73) Assignees: The Regents of the University of California, La Jolla, CA (US); Virginia Tech Intellectual Properties, Inc., Blacksburg, VA (US)

( * ) Notice: Subject to any disclaimer, the term of this patent is extended or adjusted under 35 U.S.C. 154(b) by 0 days.

(21) Appl. No.: 09/692,623

(22) Filed: Oct. 20, 2000

Related U.S. Application Data

(62) Division of application No. 09/091,521, filed as application No. PCT/US97/23032 on Dec. 5, 1997, now Pat. No. 6,149,920.

(51) Int. Cl.[7] ................................................ A61K 39/02

(52) U.S. Cl. ................................ 424/252.1; 424/184.1; 424/234.1; 424/248.1; 424/261.1; 424/200.1; 435/69.1; 435/69.3; 435/172.3; 435/320.1; 435/243; 435/252.3

(58) Field of Search ........................... 424/184.1, 234.1, 424/248.1, 261.1, 200.1, 252.1; 435/69.1, 69.3, 172.3, 320.1, 243, 252.3

(56) References Cited

U.S. PATENT DOCUMENTS

| | | | |
|---|---|---|---|
| 4,888,170 | A | 12/1989 | Curtiss, III |
| 5,468,485 | A | 11/1995 | Curtiss, III |
| 5,747,028 | A | 5/1998 | Calderwood et al. |
| 6,036,953 | A | 3/2000 | Ryan et al. |
| 6,043,057 | A | 3/2000 | Holmgren et al. |
| 6,149,920 | A | 11/2000 | Boyle et al. |
| 6,180,112 | B1 * | 1/2001 | Highlander et al. |
| 6,338,952 | B1 | 1/2002 | Young |

FOREIGN PATENT DOCUMENTS

| | | |
|---|---|---|
| WO | 94/19471 | * 9/1994 |

OTHER PUBLICATIONS

Norman F. Cheville et al., "Effects Of Age At Vaccination On Efficacy Of *Brucella abortus* Strain RB51 To Protect Cattle Against Brucellosis,", Am. J. Vet. Res., vol. 57, No. 8, pp. 1153–1156, Aug. 1996.
Mark G. Stevens et al., "Lymphocyte Proliferation in Response to *Brucella abortus* RB51 and 2308 Proteins in RB51–Vaccinated or 2308–Infected Cattle," Infection and Immunity, vol. 64, No. 3, pp. 1007–1010, Mar. 1996.
P.H. Elzer et al., Antibody–mediated protection against *Brucella abortus* in BALB/c mice at successive periods after infection: variation between virulent strain 2308 and attenuated vaccine strain 19, Immunology, vol. 82 pp. 651–658, 1994.
Mark G. Stevens et al., "Role Of Immune Responses To A GroEL Heat Shock Protein In Preventing Brucellosis In Mice Vaccinated With *Brucella abortus* Strain RB51," Comp. Immun. Microbiol. Infect. Dis. vol. 20, No. 2. pp. 147–153, Feb. 1997.
Boschiroli, M.L. et al., Protection Against Infection in Mice Vaccinated with a *Brucella abortus* Mutant, Infection and Immunity, vol. 65, No. 2, pp. 798–800, Feb. 1997.

Ramesh Vamulpalli "Overexpression of Protective Antigen as a Novel Approach to Enhance Vaccine Efficacy of *Brucella abortus* Strain RB51" Infection and Immunity, vol. 68, No. 6, Jun. 2000, p. 3286–3289.

Ramesh Vamulpalli "*Brucella abortus* Strain RB51 as a Vector for Heterologous Protein Expression and Induction of Specific Th1 Type Immune Responses" Infection and Immunity, vol. 68, No. 6, Jun. 2000, p. 3290–3286.

Sanchez et al. PNAS 86:481–485 (1989) National Academy of Sciences, Washington, D.C., USA.

Sanchez et al. *FEBS Lett.* 241:110–114 (1988) Elsevier Science B.V. Oxford, United Kingdom.

Lebens et al. *Bio/Technology* 11:1574–1578 (1993).

Bârzu et al., *Infection and Immunity* 64:4:1190–1196 (1996).

J.B. Kaper et al., "New and Improved Vaccines Against Chlorea", New Generation Vaccines , 2nd Edition, Chap.33:447–468 (1997), Marcel Dekker, Inc., New York.

J. Osek et al., "Improved Medium for Large–Scale Production of Recombinant Cholera Toxin B Subunit for Vaccine Purposes", J. Microbio. Methods, 24:117–123 (1995), Elsevier Science B.V.

N. Dhar et al., "Recombinant BCG Approach for Development of Vaccines: Cloning and Expression of Immunodominant Antigens of *M. tuberculosis",* FEMS Microbiology Letters, 190:309–316 (Sep. 15, 2000), Elsevier Science B.V.

M. Das et al., "Antisera to Selected Outer Membrane Proteins of *Vibriio cholerae* Protect Against Challenge with Homologous and Heterologous Strains of *V. cholerae*", FEMS Immunology and Med. Microbiol. 22 :303–308 (1998).

(List continued on next page.)

*Primary Examiner*—Jennifer E. Graser
(74) *Attorney, Agent, or Firm*—Burns, Doane, Swecker & Mathis, L.L.P.

(57) ABSTRACT

This invention relates to an over-expressing homologous antigen vaccine, a method of producing the same, and use of the vaccine for prophylaxis or treatment of vertebrates at risk of or suffering from disease caused by a pathogenic micro-organism. The vaccine is an attenuated or avirulent pathogenic micro-organism that over-expresses at least one homologous antigen encoded by at least one gene derived from the pathogenic micro-organism, and may also express a heterologous antigen.

11 Claims, 3 Drawing Sheets

OTHER PUBLICATIONS

H.T. Boesen et al., "*Vibrio anguillarum* Resistance to Rainbow Troup (*Oncorhynchus mykiss*) Serum: Role of O–Antigen Structure of Lipopolysaccharide", Infection and Immunity, vol. 67, No. 1, p. 294–301 (Jan. 1999), Am Society for Microbio.

A. Chernyak et al., "Induction of Protective Immunity by Synthetic *Vibrio cholerae* Hexasaccharide Derived from *V. cholerae* O1 Ogawa Lipopolysaccharide Bound to a Protein Carrier", The Journal of Infectious Diseases; 185:950–62 (2002), The Infectious Diseases Society of America.

N. Dhiman et al., "Mycobacterial Proteins—Immune Targets for Antituberculous Subunit Vaccine", Indian Journal of Experimental Biology, vol. 37:1157–1166, (Dec. 1999).

C. Hetzel et al., "An Epitope Delivery System for Use with Recombinant Mycobacteria", Infec. and Immun., vol. 66, No. 8:3643–3648, (Aug. 1998) Am Society for Microbio.

J. Holmgren et al., "Mechanisms of Disease and Immunity in Cholera: A Review", The Journal of Infectious Diseases, vol. 136 Supplement (Aug. 1977).

M.A. Horwitz et al., "Recombinant bacillus Calmette—Gurein (BCG) vaccines Expressing the *Mycobacterium tuberculosis* 30–kDa Major Secretory Protein Induce . . . " PNAS vol. 97, No. 25:13853–13858, (Dec. 5, 2000).

Z. Kossaczka et al., "Evaluation of Synthetic Schemes to Prepare Immunogenic Conjugates of *Vibrio cholerae* O139 Capsular Polysaccharide With Chicken Serum Albumin", Glycoconjugate Journal 17, 425–433 (2000), Kluwer Academic Publishers.

E. Medina et al., "Use of Live Bacterial Vaccine Vectors for Antigen Delivery: Potential and Limitations", Vaccine 19:1573–1580 (2001), Elsevier Science Ltd.

M.D. Meeks et al., "Immune Response Genes Modulate Serologic Responses to *Vibrio cholerae* TopA Pilin Peptides", Infec. and Immun., vol. 69, No. 12:7687–7694, (Dec. 2001), American Society for Microbiology.

A.S. Pym et al., "Recombinant BCG Exporting ESAT–6 Confers Enhanced Protection Against Tuberculosis", NatureMedicine, vol. 9., No. 5:533–539 (May 2003).

A.E. Toranzo et al., "Immunization with Bacterial Antigens: Vibrio Infections", Developments in Biol. Stand., vol. 90:93–105 (1997).

C. Zheng et al., "Recombinant *Mycobacterium bovis* BCG Producing the Circumsporozoite Protein of *Plasmodium falciparum* . . . ", *Parasitology International* 51:1–7 (2002), Elsevier Science Ireland Ltd.

P. Elzer et al., "Characterization 1–30 and genetic complementation of a *Brucella abortus* high–temperature–requirement A (htrA) deletion mutant", Infection & Immunity 62 No. 10:4135–4139 (Oct. 1994).

* cited by examiner

FIG. 1

Brucella spp. → Brucella DNA → Gene encoding antigen

Ligate ↓

Multicopy plasmid encoding antigen

+ Brucella vaccine strain → Transformed Brucella vaccine strain

↓

Over-expressing homologous antigen vaccine against *Brucella* spp.

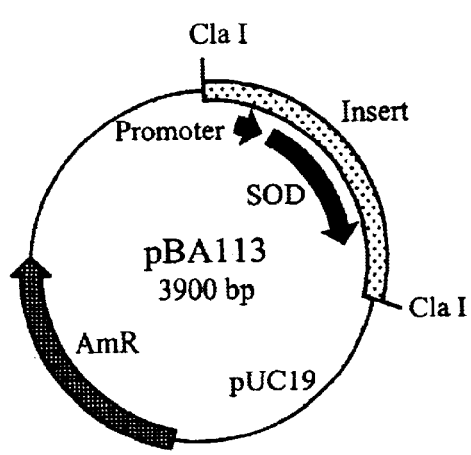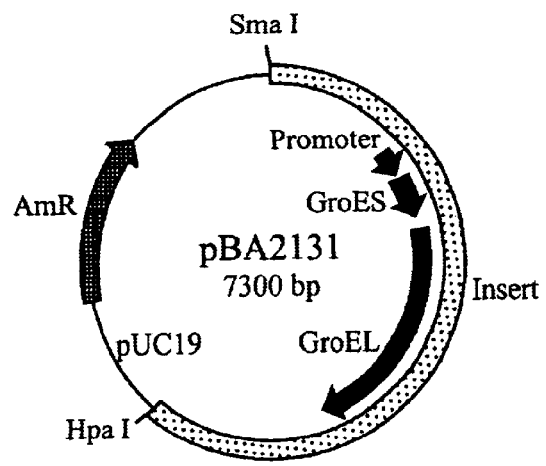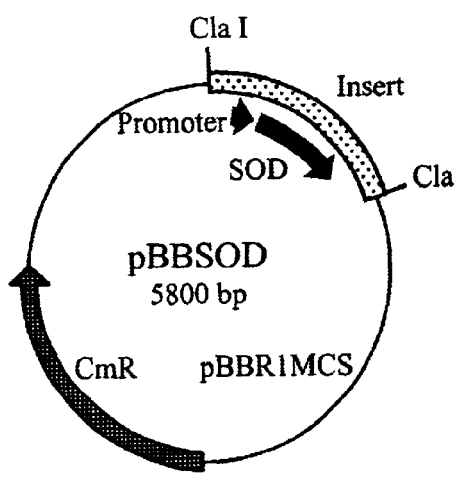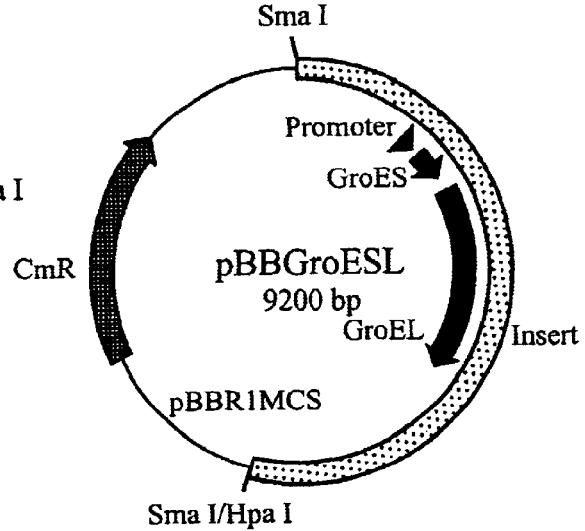
FIG. 2A FIG. 2B

OVER-EXPRESSING HOMOLOGOUS ANTIGEN VACCINE AND A METHOD OF MAKING THE SAME

This application is a divisional of Application No. 09/091,521, filed Jun. 19, 1998, now U.S. Pat. No. 6,149,920 issued Nov. 21, 2000, which is a national stage application of PCT/US97/23032 filed Dec. 5, 1997.

The invention described herein was made under a grant from the United States Department of Agriculture. Therefore, the U.S. government may have certain rights in this invention.

The invention pertains to an over-expressing homologous antigen vaccine, a method of producing the same, and a method of using the vaccine for prophylaxis or treatment of a vertebrate suffering from or at risk from a pathogen. The vaccine is derived from an attenuated or avirulent version of the pathogen, and over-expresses one or more genes from the pathogen, thereby providing immunity greater than that induced by a vaccine of the same pathogen without over-expression of a gene.

BACKGROUND OF THE INVENTION

Vaccines are used to protect against diseases, which are caused by pathogens. These pathogens are microbial organisms, such as bacteria and viruses, which affect animals, including humans. Vaccines are primarily derived from a pathogen by producing and administering either: a) an attenuated or avirulent version of the pathogen; b) the killed pathogen; c) extracted protective antigens or antigen mixes of the pathogen (homologous antigens); or d) a micro-organist expressing one or more protective antigens encoded by cloned genes originating in a microbial pathogen different from the vaccine strain (heterologous antigens).

Vaccines for both bacteria and viruses are engineered from microorganisms expressing one or more protective antigens, as described by K. Jones and M. Sheppard in Designer Vaccines, CRC Press (1997). Vaccines are intended to produce an immune response in the recipient consisting of at least one of an antibody mediated or T cell mediated immune response, thereby preventing future infection by a pathogen, or fighting a current pathogenic infection. In particular, vaccines against facultative intracellular pathogens, those growing inside the cells of the infected host, need to induce a strong and appropriate cell mediated immune response. In contrast, vaccines against obligate extracellular pathogens need to induce an appropriate antibody mediated immune response. Often, regardless of the pathogen, an appropriate combined antibody and cellular mediated immune response leads to sufficient protection or relief from infection. In order to achieve this protection or relief from infection, vaccines may express one or more homologous antigens, heterologous antigens, or a combination of both.

Vaccines may be administered to vertebrates both to prevent and treat infection by pathogens. Thus, vaccines are frequently administered to prevent the spread of a disease caused by a pathogen. In particular, herd animals, such as cows, goats, sheep and swine, are often vaccinated to prevent the spread of a disease among members of the herd. Further, because certain diseases may travel between vertebrates, including travel between various animals and between animals and humans, vaccines are used to prevent the spread of disease between various species, usually by administration to the infected animal and other uninfected animals in the immediate vicinity. However, other animals in the area which are less likely to contract the disease may also be vaccinated as a prophylactic measure. For example, an infected cow and its as yet uninfected herd may be vaccinated to treat a disease and prevent its further spread. As a prophylactic measure, other animals which are likely to contract the disease from the infected cow, such as neighboring cows, sheep or humans, may be vaccinated as well.

It has been found that vaccines derived from an attenuated or avirulent version of a pathogen are highly effective in preventing or fighting disease caused by that pathogen. In particular, it is known that such attenuated or avirulent pathogens can be modified to express heterologous antigens (antigens which are derived from a pathogen of a different species). In order to express heterologous antigens in a desired attenuated or avirulent pathogen, a gene encoding an antigen capable of providing protection against the pathogen is identified from the deoxyribonucleic acid of a heterologous species. The desired gene is isolated and then inserted into a plasmid capable of replication and expression in the attenuated or avirulent pathogen. The plasmid is then introduced into the attenuated or avirulent pathogen, and causes expression of the heterologous antigen upon administration to a subject vertebrate.

An example of such expression of an heterologous antigen is the bacterial vaccine Salmonella, which expresses a Streptococcus spaA protein. See U.S. Pat. No. 4,888,170. This vaccine comprises an avirulent derivative of a pathogenic microbe of the genus Salmonella, which in turn expresses a recombinant gene derived from a pathogen of the species Streptococcus mutans, thereby producing an antigen capable of inducing an immune response in a vertebrate against the pathogen.

A further example of heterologous expression is *Vibrio cholera* vaccines. A number of live attenuated strains of *Vibrio cholera* have been developed to vaccinate humans against cholera. See Kaper, J. B., et al., New and improved vaccines against cholera in New Generation Vaccines (eds. MM Levin et al.) Marcel Deker, Inc., NY, 1997. Some of these strains over-express heterologous antigens. See Butterton, J. R. and S. B. Calderwood, Attenuated *Vibrio cholera* as a live vector for expression of foreign antigens in New Generation Vaccines (eds. MM Levin et al.) Marcel Deker, Inc., NY, 1997. The immunity induced by the attenuated vaccine strains is the result of inducing antibodies which have either antibacterial and/or antitoxic activities. Some strains have been attenuated by the deletion of a number of genes encoding toxigenic components, including the A subunit of the cholera toxin encoded by the ctxA gene. However, in order for a cholera vaccine strain to be fully protective, it is necessary that the ctxb gene encoding the B subunit (to which the A subunit binds) be expressed to allow for the production of antibodies that neutralize the cholera toxin. The ctxB gene has been over-expressed in Vibrio cholera for the purpose of producing large amounts of the antigen cholera toxin 2 (CTB). The over-expressed antigen CTB is collected, purified and used as a subunit vaccine which is the extracted CTB antigen. See Lebens M., et al., 1993, Biotechnology (NY) Dec; 11:1574–1578. However, although an over-expressed antigen has itself been used as a vaccine, an attenuated or avirulent pathogen of *Vibrio cholera* which over-expresses the ctxB gene, or any other homologous gene, has not been used as a live vaccine.

Another example of heterologous expression is in Mycobacterium spp. vaccines, used to prevent tuberculosis in humans. The *Mycobacterium tuberculosis* GroEL protein induces protective immunity when expressed by the groEL gene transfected into macrophages (Silva, C. L. and Lowrie, D. B., 1994, Immunology 84:244–248), indicating that GroEL protein is a protective antigen if presented to T cells by this type of antigen presenting cell (APC). Naked DNA vaccines using Mycobacterium genes coding for a variety of antigens (hsp70, 85 kDa, 65 kDa, 36 kDa, 6 kDa) are also able to induce protective immunity. See Lowrie, D. B. et al., 1997, Vaccine 15:834–838; Tascon, E. et al., 1996, Nat. Med. 2:888–892; and Lozes, E. et al., 1997, Vaccine 15:880–833. It is believed that the naked DNA vaccines work because they transfect APCs (Chattergon, M. et al., 1997, FASEB J. 11:753–763.) which in turn present the antigen appropriately to T cells, thereby inducing a protective cell mediated immunity. *M. bovis* BCG, a live, attenuated strain of Mycobacterium, is used to induce protective immunity against *M. tuberculosis* infection in humans. Fine, PM. 1988, Br. Med. Bull. 44:91.

Antigen vaccines developed against Brucellosis provide examples of homologous-antigen expression, wherein the antigen is derived from the same species as the attenuated pathogen. Brucellosis is an infectious bacterial disease which can be transmitted to human beings by animals. It is caused by any of a variety of species of pathogenic aerobic bacteria of the genus Brucella. In animals, Brucellosis can result in abortion and infertility. In humans, it causes fever, malaise and headaches. This disease has been extensively studied, resulting in the development of numerous vaccines.

It is known that existing vaccine strains of Brucella, such as *B. abortus* strains 19 and RB51, and *B. melitensis* strain REV1, can both protect against the Brucella species from which they were derived and cross protect against infection by other species, such as *B. abortus, B. melitensis, B. ovis, B. suis, B. canis* and *B. neotomae*. See Winter, A. J. et al., 1996, Am. J. Vet. Res., 57:677; P. Nicoletti in *Animal Brucellosia*, CRC Press (1990), pp. 284–296; J. M. Blasco in *Animal Brucellosis*, CRC Press (1990), pp. 368–370; and G. C. Alton in *Animal Brucellosis*, CRC Press (1990), pp. 395–400. New *B. melitensis* strain VTRM1 and *B. suis* strain VTRS1 also cross protect against various Brucella species. Al Winter, A. J. et al., *Am. J. Vet. Res.,* 57:677.

In the past, one of the most commonly used vaccines to prevent bovine Brucellosis was *B. abortus* strain 19, as described by P. Nicoletti in *Animal Brucellosis*, CRC Press (1990), pages 284–296. This particular strain of *B. abortus* provided immunity in cattle with a range of protection from 65 to 75% depending upon a number of variables, such as the age of the cattle at vaccination, the dose administered, the route of administration and prevalence of Brucellosis in the vaccinated herd.

*B. Abortus* strain RB51, a new attenuated live Brucella vaccine (marketed as RB-51®), is a stable vaccine approved for use in the United States. See Schurig, G. G. et al, 1991, *Vet. Microbiol.* 26:359; and Colby, L., 1997, M. Sc. Thesis, Virginia Tech, Blacksburg, Va. Attenuation of strain, RB51 is indicated by studies carried out in mice, goats and cattle. See Schurig, G. G., 1991, Vet. Microbiol. 28:171; Palmer R. M. et al., 1997, Am. J. Vet Res. 58:472; Roop, R. M. et al., 1995, Res. Vet. Science, 51:359; and Zambrano, A. J. et al., 1995, Archivos de Medicina Veterinaria XXVIII, No. extraordinario:119–121. In comparison to the protection provided by strain 19, strain RB51 has been shown in single vaccination protocols to be similarly protective in cattle. See Cheville, N. F. et al., 1993, Amer. J. Vet Research 53:1881; and Cheville, N. F. et al., 1996, Amer. J. Vet Research, 57:1153. Further, oral administration of strain RB51 in mice and cattle has indicated protective immunity. see Stevens, M. G. et al., 1996, Infect. Immun. 64:534. In particular, the mouse model indicates that the protective immunity to Brucellosis induced by strain RB51 is solely T cell mediated because a passive transfer of RB51-induced antibodies does not protect against the disease, whereas adoptive T cell transfer does. See Bagchi, T., 1990, M. Sc. Thesis, Virginia Tech, Blacksburg, Va.; Jimenez deBagues, M. P. et al., 1994, *Infect. Immun.* 62:4990. It is believed that vaccination with RB-51® confers protection by inducing production of interferon gamma able to activate macrophages and specific cytotoxic T cells in the subject which are able to kill Brucella infected macrophages.

Although RB-51®, derived from *B. abortus* strain 2308, is the best current vaccine against Brucellosis in animals, it is still not 100% effective. None of the current Brucellosis vaccines are totally effective.

Therefore, research continues on promising strains, such as *B. abortus* strain RB51. For example, expression of heterologous antigens by *B. abortus* strain RB51 has been described byS. Cravero, et al., 1995, Proceedings 4th Intl. Vet. Immunol. Symposium, July, Davis, Ca., Abstract # 276; and S. Cravero et al., 1996, Conference of ResearchWorkers in Animal Diseases, Nov., Chicago, Abstract # 150. Overexpression of a homologous antigen by Brucella has been described as a research tool for the purpose of complementing specific deletion mutants for the study of HtrA protein in *B. abortus* (P. H. Elzer, Inf. Immun., 1994, 62:4131), and for the study of physiological functions as discussed by R. Wright at an Oral Presentation of the Brucella Research Conference on Nov. 9, 1997 in Chicago, Ill.

However, over-expression of homologous antigens of Brucella or other pathogens, with or without concomitant expression of a heterologous antigen, has not been studied for use in vaccines. Over-expression of homologous antigens previously has been used primarily as a research tool, as described above. An attenuated or avirulent pathogen modified to over-express an homologous antigen has not been used as a live vaccine. However, we have found that a vaccine which is an attenuated or avirulent pathogen which over-expresses one or more homologous antigens, as described herein, will provide greater protection against a pathogenic disease than vaccines of attenuated pathogens which express wild type levels of the same homologous antigens.

Therefore, the invention is directed to a vaccine, a means of producing the vaccine, and its use for prophylaxis and treatment of a pathogenic disease wherein the vaccine is an attenuated or avirulent pathogen which over-expresses at least one homologous antigen, thereby providing greater protection against and treatment of the disease caused by the unattenuated pathogen in the subject vertebrate.

SUMMARY OF THE INVENTION

The invention is directed to a live vaccine which is an attenuated or avirulent pathogen which over-expresses one or more homologous antigens of a pathogen, a method of producing the same, and a method of treating animals, including humans, with the vaccine. This vaccine increases the level of protection against the unattenuated pathogen in comparison to vaccines of attenuated pathogens expressing wild type levels of homologous antigens of the pathogen. In this manner, the over-expressing homologous antigen vaccine will induce a strong cellular mediated immune response and/or a strong humoral antibody response against the unattenuated pathogen in the vaccinated subject.

In particular, it is the purpose of this invention to provide a method of producing a vaccine which is an attenuated or avirulent pathogen over-expressing a homologous antigen, and immunizing an animal, including humans, with the vaccine such that the vaccine induces a strong cell mediated or antibody mediated immune response against a virulent pathogen, thereby providing complete protection, such as sterile immunity, against a challenge by the virulent pathogen.

It is a further object of the invention to provide a method of producing a vaccine which is an attenuated or avirulent pathogen over-expressing a homologous antigen, and immunizing an animal with the vaccine such that the vaccine causes over-expression of an homologous antigen and expression of a heterologous antigen, both of which provide protection against the virulent pathogen in the vaccinated subject.

It is yet a further object of this invention to provide an over-expressing homologous vaccine, a means for making such a vaccine and a method of using the vaccine for prophylaxis and treatment of Brucellosis in animals, especially bovine animals.

BRIEF DESCRIPTION OF THE DRAWINGS

The attached figures are intended to aid in explaining and to more particularly point out the invention described herein. In particular:

FIG. 1 is a diagram depicting the derivation of a homologous antigen from a Brucella species, and insertion of the antigen into a Brucella species vaccine strain;

FIG. 2 depicts construction of recombinant plasmids for over-expression of copper/zinc SOD(A) and GroES and GroEL(B) in *B. abortus* strain RB51;

DETAILED DESCRIPTION

Figure 3:
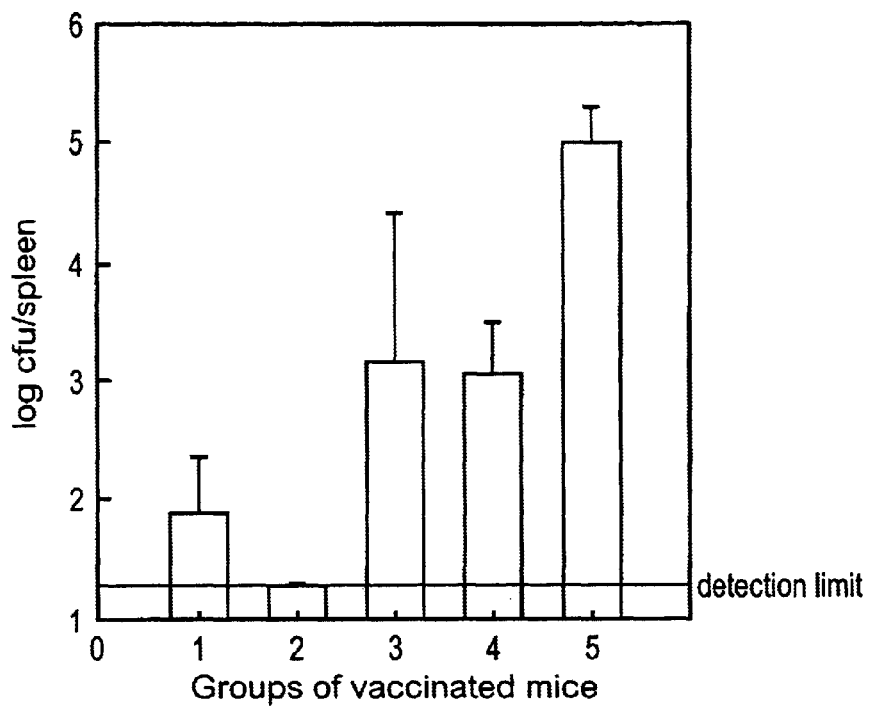
FIG. 3 demonstrates the clearance of *B. abortus* strain 2308 from the spleens of mice vaccinated with *B. abortus* strain RB51 over-expressing copper/zinc SOD or GroES/EL.

The invention is directed to a vaccine for the immunization of vertebrates against disease caused by a pathogen, wherein the vaccine comprises an attenuated or avirulent pathogen that over-expresses one or more homologous antigens encoded by at least one gene from the pathogen, wherein each antigen is capable of inducing a protective immune response against the pathogen.

This over-expressing homologous antigen vaccine is produced by genetic engineering of live, attenuated microbes by a process having the steps of: a) selecting a gene encoding an homologous antigen capable of directly or indirectly stimulating protective immunity against a pathogenic microorganism (pathogen), and b) inserting said gene into an attenuated or avirulent version of the pathogen such that the homologous antigen is over-expressed. The resultant overexpressing homologous antigen vaccine (OHAV) is more specifically prepared by the following steps:

a) extracting deoxyribonucleic acid from a pathogenic micro-organism;

b) identifying a gene from the deoxyribonucleic acid, wherein said gene encodes at least one antigen capable of stimulating protective immunity against the pathogenic micro-organism;

c) inserting said gene into a plasmid capable of replication and expression in the pathogenic micro-organism; and d) introducing said plasmid into an attenuated or avirulent version of the pathogenic micro-organism.

The resultant vaccine synthesizes the antigen as a result of transcription and translation of the gene located in at least two sites, i.e., the genome and the plasmid. In particular, it is preferred that the plasmid be a multicopy type, so that it may produce a greater number of the protective antigen than the single genomic copy otherwise generated.

The above method may be used to create over-expressing expressing homologous antigen vaccines for many different diseases. The over-expression of the antigen usually increases both the T cell and antibody immune response, thereby greatly increasing the level of protection in the subject. Because both types of immune response are improved, both intracellular and extracellular pathogens are affected, thereby providing greater protection against the pathogen.

For example, a vaccine against the pathogenic microorganism Brucella may be produced. In particular, the pathogen may be selected from any species of Brucella, including *B. abortus, B. melitensis, B. ovis, B. suis, B. canis* and *B. neotomae*. The pathogen used to produce the vaccine is preferably selected from a specific strain of Brucella, such as *B. abortus* strain 19, *B. abortus* strain RB51, *B. melitensis* strain VTRM1, *B. suis* strain VTRS1 and *B. melitensis* strain REV1.

It is particularly advantageous that the vaccine be prepared with one or more of a Cu/Zn SOD gene, a GroES gene or a GroEL gene of *B. abortus* strain RB51. In particular, it is preferred that the above genes be obtained from a pUC19 genomic library of *B. abortus* strain 2308.

A vaccine produced according to the above specifications is particularly effective for prophylaxis or treatment of diseases such as Brucellosis. For example, an effective vaccine for prophylaxis or treatment of a bovine animal against Brucellosis according to the invention is an attenuated or avirulent derivative of *B. abortus* strain RB51 capable of over-expressing at least one homologous antigen. In particular, it is preferred that the antigen be encoded by one or more of a Cu/Zn SOD gene, a GroES gene or a GroEL gene, preferably selected from a pUC19 genomic library of *B. abortus* strain 2308. It is even more preferable that the attenuated or avirulent derivative also express a heterologous antigen capable of inducing protective immunity against *B. abortus*.

The method of prophylaxis or treatment of a vertebrate suffering from a pathogenic micro-organism is as follows:

a) extract deoxyribonucleic acid from the pathogenic micro-organism;

b) identify at least one gene encoding at least one antigen from the deoxyribonucleic acid, wherein the antigen is capable of stimulating protective immunity against the pathogenic micro-organism;

c) insert the at least one gene into a plasmid capable of replicating and expressing in the pathogenic micro-organism;

d) transform an attenuated or avirulent version of the pathogenic micro-organism with the plasmid to form a vaccine; and e) administer an effective amount of the vaccine to the vertebrate. The vaccine used for the method for prophylaxis and treatment may be an original vaccine strain or a modified existing vaccine strain. For example, *B. abortus* strain RB51 can be modified to over-express a homologous antigen, thereby producing a new strain capable of use in a vaccine for the prophylaxis or treatment of Brucellosis, particularly in bovine animals.

In particular, a new Brucella vaccine can be prepared by: 1) selecting a gene encoding a protective antigen from a strain of Brucella; 2) inserting the gene from the pathogen into a multicopy plasmid capable of replication and expression in Brucella; and 3) introducing the plasmid into Brucella by means such as transformation. One or more homologous antigens may be over-expressed in this manner. Additionally, one or more heterologous antigens may be expressed in the vaccine by methods known in the art.

By over-expressing one or more homologous antigens of a given pathogen, greater T cell and/or antibody immune response against that pathogen is stimulated in the vertebrate treated with the vaccine produced from the attenuated or avirulent pathogen, affording greater protection against the unattenuated pathogen. Further protection may be offered by additional expression of one or more heterologous antigens by the attenuated or avirulent pathogen by means known to one of ordinary skill in the art.

The resultant over-expressing homologous antigen vaccine may be administered in a dose effective to promote prophylaxis or treatment of a disease caused by the pathogen in the desired subject vertebrate. As known to one of ordinary skill in the art, dosages should be adjusted for each subject based on factors such as weight, age, and environmental factors. The effective dose may be administered in any effective manner based on the type of animal being treated, its age and condition.

EXAMPLES

Example 1

Two OHAVs were constructed by over-expressing either the Cu/Zn SOD gene or the GroES and GroEL genes in *B. abortus* strain RB51. The genes for Cu/Zn SOD, GroES and GroEL were initially obtained from a pUC19 genomic library of *B. abortus* strain 2308. As shown in FIG. 2, the inserts containing these genes along with their own promoters were excised from the pBA113 (SOD) and pBA2131 (GroES and GroEL) regions and subcloned into pBBR1MCS, a broad-host range plasmid which has routinely been used in Brucella research. The resulting recombinant plasmids were termed as pBBSOD and pBBGroES/EL (FIG. 2). The *B. abortus* strain RB51 was transformed with these plasmids by electroporation. Brucella containing the plasmids were selected by plating the transformed bacteria on trypticase soy agar plates containing 30 $\mu$Ag/mL of chloramphenicol. To determine the over-expression of the cloned genes, the antibiotic resistant colonies were individually grown in trypticase soya broth and the bacterial extracts used as antigens in an immunoblot analysis. Strain RB51 containing pBBSOD (RB51SOD) and pBEGroES/EL (RBSlGroESL) over-expressed Cu/zn SOD and GroEL, respectively, as compared to strain RB51 containing PBBR1MCS alone (RB51pBB).

Protection studies in mice:

Groups of 8 mice were vaccinated by inoculating, intraperitoneally, $4\times10^8$ colony forming units (cfu) of either strain RB51SOD, RB51GroESL, RB51pBB or RB51 in 0.5 mL of saline. One group of mice was inoculated with 0.5 mL of saline as a control. After 6 weeks, 5 mice in each group were challenged intraperitoneally with $2.5\times10^4$ cfu of virulent strain 2308. The remaining three mice in each group were used to characterize the immune responses. Two weeks after challenge with virulent strain 2308, mice were euthanized and the cfu of strain 2308 per spleen were determined. Mice immunized with strain RB51SOD had a significantly lower number of bacteria as compared to those immunized with strain RB51. In mice immunized with strain RB51GroESL, the number of bacteria observable was at the lower limit (<20 cfu/spleen) of the detection method.

Characterization of immune responses

After 6 weeks of vaccination, serum was collected from 3 mice in each group for analysis of the humoral antibody response. These mice were euthanized and the lymphocytes harvested from their spleens were used to study the cell-mediated immune response. As shown in FIG. 3, mice-vaccinated with strain RB51 developed antibodies to GroEL but did not develop antibodies to Cu/Zn SOD. In contrast, mice vaccinated with strain RB51SOD developed a strong antibody response to Cu/Zn SOD, and mice vaccinated with strain RB51GroESL developed a stronger antibody response to GroEL protein (FIG. 3) than that exhibited by strain RB51 vaccinated mice. These results indicate an enhanced antibody response by the OHAV.

Figure 4:
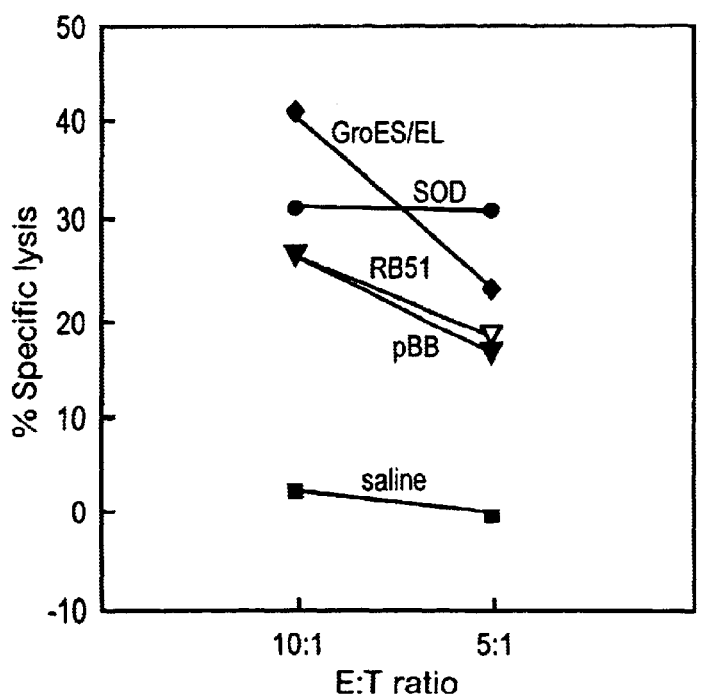
FIG. 4 demonstrates the cytotoxic activity by lymphocytes toward Brucella infected cells from mice vaccinated with *B. abortus* strain RB51 over-expressing copper/zinc SOD or GroES/EL.

The cell mediated immune response caused was characterized by determining the cytotoxic activity of lymphocytes toward Brucella infected cells. Specific splenic lymphocyte activity was enhanced in vitro by co-culturing with mitomycin C treated Brucella infected macrophages as stimulator cells. A cytotoxicity assay was performed using enhanced lymphocytes as effector cells (E) and Brucella infected macrophages as target cells (T). In the assay, E and T cells were mixed in two different ratios., 10:1 and 5:1. The percent specific lysis of target cells was calculated for each E:T ratio using standard methods (FIG. 4). Lymphocytes from mice vaccinated with RB51SOD or RB51GroESL showed enhanced cytotoxic activity relative to saline or strain RB51 vaccinated mice. This increased cytotoxic lymphocyte activity (indicated by the increased % specific lysis) directly correlates with the observed enhanced protection of mice against challenge with virulent *B. abortus* strain 2308; the higher the protective level, the higher the specific cytotoxic activity.

Example 2

An OHAV is constructed by over-expressing the ctxB gene in Vibrio cholera. The gene is obtained from the deoxyribonucleic acid of the pathogen and inserted into a plasmid capable of replicating and expressing in the pathogen. The resulting recombinant plasmid is used to transform Vibrio cholera by means of electroporation. Plasmids are plated and selected by means known in the art. The resultant over-expressing homologous antigen vaccine strain promotes overproduction of antibodies that neutralize the cholera toxin, thereby providing greater protection for prophylaxis and treatment of cholera in cholera in humans.

Example 3

An OHAV is constructed by over-expressing the groEL gene of *Mycobacterium tuberculosis* in a Mycobacterium species. The gene is obtainedfrom the deoxyribonucleic acid of the pathogen and inserted into a plasmid capable of replicating and expressing in the pathogen. The resulting recombinant plasmid is used to transform a Mycobacterium species by means of electroporation. Plasmids are plated and selected by means known in the art. The resultant over-expressing homologous antigen vaccine strain promotes overproduction of GroEL proteins, thereby providing greater protection for prophylaxis and treatment of tuberculosis in humans. In particular, over-expression of the qroEL gene encoding the GroEL protein in *M. bovis* BCG provides greater protective immunity against tuberculosis because BCG vaccines are known to target antigen protecting cells, such as macrophages, thereby providing a means of introducing the antigens into the T cells, inducing protective cell mediated immunity.

The above examples are illustrative only. The scope of the invention is not limited to the examples, but is described in the specification and accompanying claims. Those of ordinary skill in the art will recognize methods and materials which could be substituted for those described above, and any such methods and materials are intended to be covered by the above disclosure and following claims.

We claim:

1. A method for immunization, prophylaxis or treatment of a vertebrate at risk of or suffering from Brucellosis comprising the steps of:
    a) extracting deoxyribonucleic acid from Brucella;
    b) identifying at least one gene encoding at least one homologous antigen from the deoxyribonucleic acid wherein said at least one homologous antigen induces protective immunity against Brucella;
    c) inserting the at least one gene into a multicopy plasmid capable of replicating and expressing in Brucella;
    d) transforming an attenuated or avirulent strain of Brucella with the plasmid to form a vaccine; and
    e) administering an effective amount of said vaccine to the vertebrate, wherein Brucella is *B. abortus, B. melitensis, B. suis, B. ovis, B. neotomae* or *B. canis*.

2. The method of claim 1, wherein the attenuated or avirulent strain of Brucella is *B. abortus* strain RB51.

3. The method of claim 2, wherein the at least one gene is a Cu/Zn SOD gene.

4. The method of claim 2, wherein the at least one gene is one or both of a GroES gene and GroEL gene.

5. A method for imiunition, prophylaxis or treatment of a vertebrate at risk of or suffering from Brucellosis comprising the steps of:
    a) extracting deoxyribonucleic acid from Brucella;
    b) identifying at least one gene encoding at least one homologous antigen from the deoxyribonucleic acid wherein said at least one homologous antigen induces protective immunity against Brucella;
    c) inserting the at least one gene into a multicopy plasmid capable of replicating and expressing in Brucella;
    d) transforming an attenuated or avirulent strain of Brucella with the plasmid to form a vaccine; and
    e) administering an effective amount of said vaccine to the vertebrate, wherein the attenuated or avirulent strain of Brucella is *B. abortus* strain RB51.

6. The method of claim 5, wherein the at least one gene is a Cu/Zn SOD gene.

7. The method of claim 5, wherein the at least one gene is one or both of a GroES or a GroEL gene.

8. The method of claim 1, wherein the attenuated or avirulent strain of Brucella further expresses one or more heterologous antigens.

9. The method of claim 1, wherein the vertebrate is a bovine.

10. The method of claim 5, wherein the *B. abortus* strain RB51 further expresses one or more heterologous antigens.

11. The method of claim 5, wherein the vertebrate is a bovine.

* * * * *